Figure 1A:
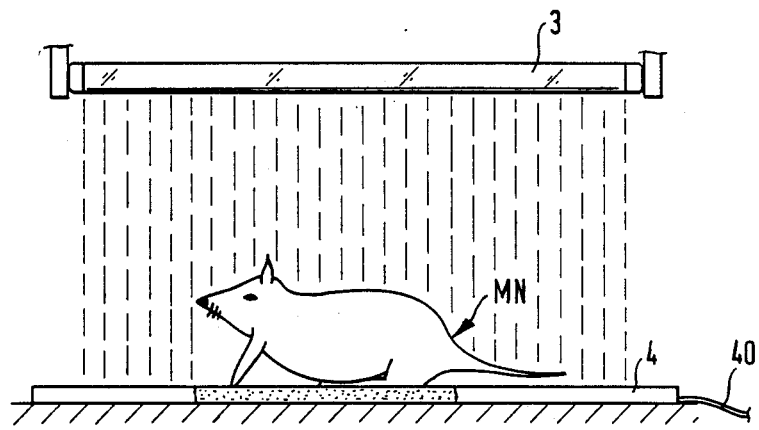

United States Patent [19]

Brom et al.

[11] Patent Number: 4,917,117

[45] Date of Patent: Apr. 17, 1990

[54] PROCESS AND APPARATUS FOR THE RECORDING AND/OR EVALUATION OF THE MOVEMENT BEHAVIOR OF EXPERIMENTAL ANIMALS

[75] Inventors: Richard Brom, Habsheim/Brübach, France; Alfred Schweizer, Basel; Werner Bichsel, Muttenz, both of Switzerland

[73] Assignee: Ciba-Geigy Corporation, Ardsley, N.Y.

[21] Appl. No.: 91,004

[22] Filed: Aug. 31, 1987

[30] Foreign Application Priority Data

Sep. 4, 1986 [CH] Switzerland ................. 3560/86

[51] Int. Cl.[4] .............................. A61B 5/10
[52] U.S. Cl. .................. 128/782; 128/665
[58] Field of Search ........... 128/782, 665; 340/573; 250/221

[56] References Cited

U.S. PATENT DOCUMENTS

| | | | |
|---|---|---|---|
| 3,063,630 | 11/1962 | Cromley et al. | 128/782 |
| 3,378,675 | 4/1968 | Cromley | 235/92 |
| 3,494,329 | 7/1967 | Frieberger et al. | 128/782 |
| 3,549,892 | 12/1970 | Perlman | 250/221 |
| 3,703,101 | 11/1972 | Pence | 128/782 |
| 3,781,842 | 12/1973 | Campman | 250/221 |
| 4,075,507 | 2/1978 | Pauli et al. | 250/221 |
| 4,229,733 | 10/1980 | Tulenko et al. | 340/573 |
| 4,320,766 | 3/1982 | Alihanka et al. | 128/782 |
| 4,448,150 | 5/1984 | Catsimpoolas | 250/221 |
| 4,645,919 | 2/1987 | McCaleb | 250/221 |

FOREIGN PATENT DOCUMENTS

| | | |
|---|---|---|
| 2728894 | 1/1979 | Fed. Rep. of Germany . |
| 1519720 | 4/1968 | France . |
| 0140799 | 3/1980 | German Democratic Rep. ............. 128/782 |
| 0211064 | 7/1984 | German Democratic Rep. ............. 128/782 |
| 58-161806 | 9/1983 | Japan . |
| 60-213808 | 10/1986 | Japan . |
| 0843947 | 7/1981 | U.S.S.R. ............. 128/782 |

OTHER PUBLICATIONS

Medical and Biological Engineering 11, 490–498 (Jul. 1973).
Journal of Pharmacology 125, 237–240 (Sep. 1958).
Med. and Biol. Eng. and Computing., 1977, 15, 333–334, Wilcox et al.
Med. and Biol. Engineering, Nov. 1974, Smit et al.
NASA Tech. Brief No. NTN-77/0819, Winter 1976, LAR-11999, U.S.

Primary Examiner—Max Hindenburg
Assistant Examiner—Kennedy J. Schaetzle
Attorney, Agent, or Firm—Harry Falber

[57] ABSTRACT

The movement and stretching behavior of experimental animals, which is significant in different tests of the effect of drugs, is rendered objectively analyzable by the photoelectric conversion of the shadow of the animal into an electric signal. The shadow of the animal is projected onto a photoelement (4) forming a projection surface. The signal generated by the photo-element-projection surface (4) is conducted by means of a current/voltage converter (5) to an aplifier (6). The amplified signal (S) is passed on the one hand to a recorder (7) and on the other through an amplitude threshold value detector (8) and a time interval threshold value detector to a counter (9). The threshold values are set in a manner such that the counter counts only the significant stretchings of the experimental animal.

24 Claims, 7 Drawing Sheets

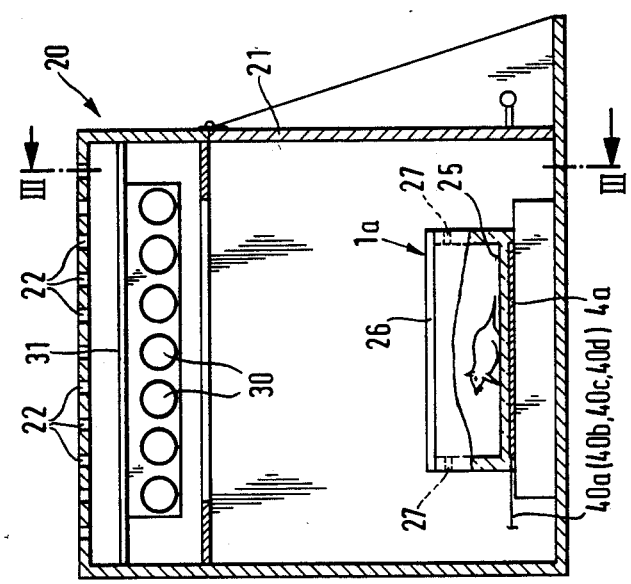
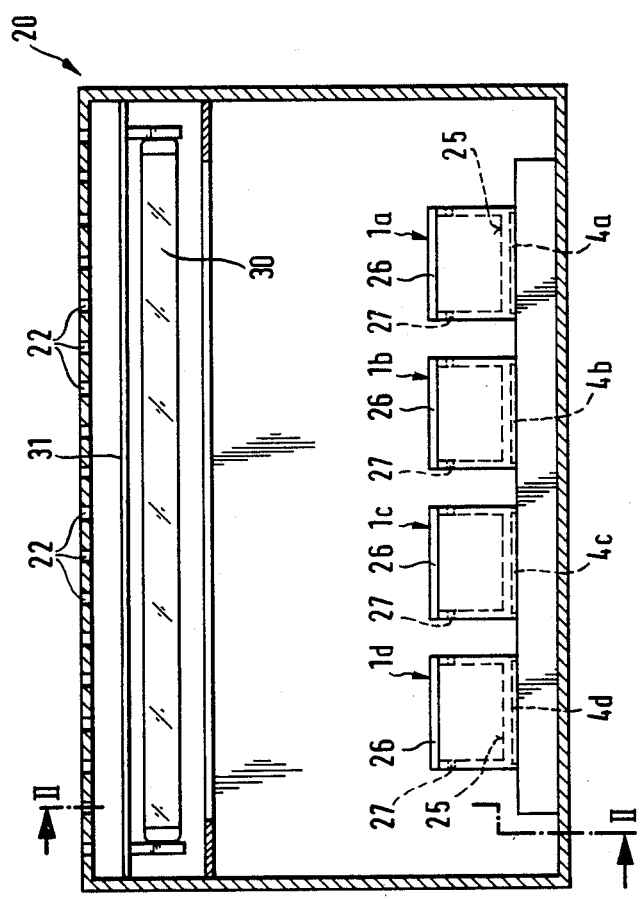

PROCESS AND APPARATUS FOR THE RECORDING AND/OR EVALUATION OF THE MOVEMENT BEHAVIOR OF EXPERIMENTAL ANIMALS

The movement and stretching behavior of experimental animals is significant for different tests. For example the stretch test (writhing test) is used to determine the pain attenuating effects of drugs. For this purpose an irritant is injected into the peritoneum of experimental animals, for example mice, which produces an inflammation causing little pain. Mice react to this irritation by pressing their spinal column downward, which presumably provides instantaneous relief. The effect of a drug can then be tested by comparing the number of stretching movements of animals treated with the drug (test substance) with the number of stretching movements of untreated animals (Journal of Pharmacology and Experimental Therapeutics, Vol. 125, No. 237, 1959, pages 237-240, L. C. Hedershot et al.). Different test preparations, in particular centrally and peripherally acting drugs, may be compared with each other in a similar manner.

Heretofore, writhing tests were monitored visually. The number of significant stretch movements are counted by means of a stop watch and recorded. Results depend very strongly on the persons performing the observations and their degree of fatigue. Subsequent controls are not possible. For this reason, the results obtained by the observers are not objective as individual human failings lead to records which are not always adequately accurate and valid. Furthermore, records produced by human observers in view of these imponderabilities frequently cannot be used subsequently as proof of the performance of tests according to regulations, in order to satisfy the steadily increasing requirements of the authorities, for example the GLP (Good Laboratory Practice) standards of the USA FDA (Food and Drug Administration).

To eliminate the disadvantages associated with the use of human observers, a process and an apparatus for the recording of the movement activity of animals by optical-optoelectronic means have already been proposed in DE-A1-2 728 894. In the process, an image of the animals to be observed is projected by means of an optical lens onto a measuring plate consisting of a plurality of photoelectric elements. The photoelectric cells are divided into four groups and are applied to a branch of a Wheatstone measuring bridge. Depending on the respective position of the one branch of the measuring bridge and of a group of associated photoelectric cells the movement of the animal in a certain direction may be determined, if the displacement of the edge of the image of the animal taking place is sufficiently large so that at least in one of the photoresistances a measurable variation of the electric current of the measuring bridge is occurring. The disadvantage here is that resolution depends on the distance and the number of the photoresistances used, for which reason usable results may be obtained only by means of an extensive wiring effort and a large number of photoresistances. Because of the matrix-like layout of the photoelectric cells, for movements with location changes, preferred directions, i.e. directions in which the determination of a movement leads to a larger current variation in another direction, are obtained. If local movements (local motility) are to be determined for the automated performance of writhing tests, such a directional sensitivity represents an interference and depending on the direction of the writhing test, leads to measuring errors.

In Medical and Biological Engineering, Vol. 11, No. 4, July 1973, pages 490 to 498, A. Cohen et al., an activity analysis system for behavior studies on small animals is described, wherein three matrix arrays are provided, each of which contains a plurality of light emitting diodes and photodetectors. The photodetectors of a matrix layout are always connected in parallel, with the output signal being passed to a threshold value detector. Because of the relatively large distances between the individual elements of the matrix arrays, a very low resolution capability is obtained, so that the use of this known activity analysis system, which may be connected with a microcomputer by means of an interface, does not allow for the determination of writhing movements of animals.

An automatic analyzer known from FR 1 519 720 for animal behavior comprises in addition to a series of mechanical and acoustic sensors, a plurality of light sources, mounted on one side wall of a cage and associated with photoelectric sensors on the opposite side, the resistance of which varies as a function of the intensity of the light received. The running away of a rat is detected in the analyzer in that the different beams of light between two photoelectric elements are interrupted, the variations of the current flowing between the photoelectric sensors being amplified by an amplifier and applied to a counter. Relatively slow, low amplitude stretch movements of an experimental animal cannot be detected.

Another apparatus for the automatic evaluation of animals treated with a drug is described in WO-A-8 604 802. With this apparatus the vertical movements of a rod exceeding a predetermined threshold value are detected, the experimental animal being tied to the rod, preferably by its tail. There is, however, no evaluation of an optical image in the microcomputer connected thereto.

It is the object of the present invention to provide a process and an apparatus making it possible to detect the writhing and movement behavior of experimental animals for recording and subsequent evaluation, optoelectronically with a high resolution and equal sensitivity in all directions, while keeping the wiring effort of the optoelectronic structural elements low even in the case of a large field of vision.

Figure 1B:
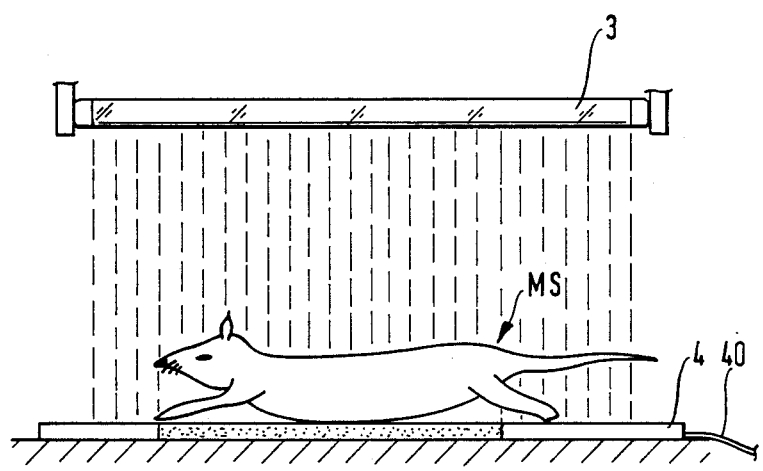
Figure 4:
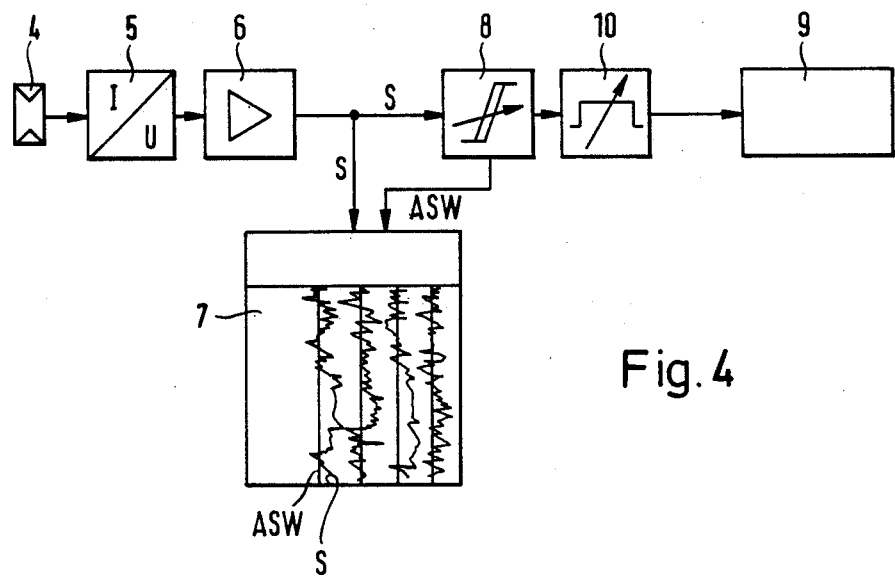
Figure 5:
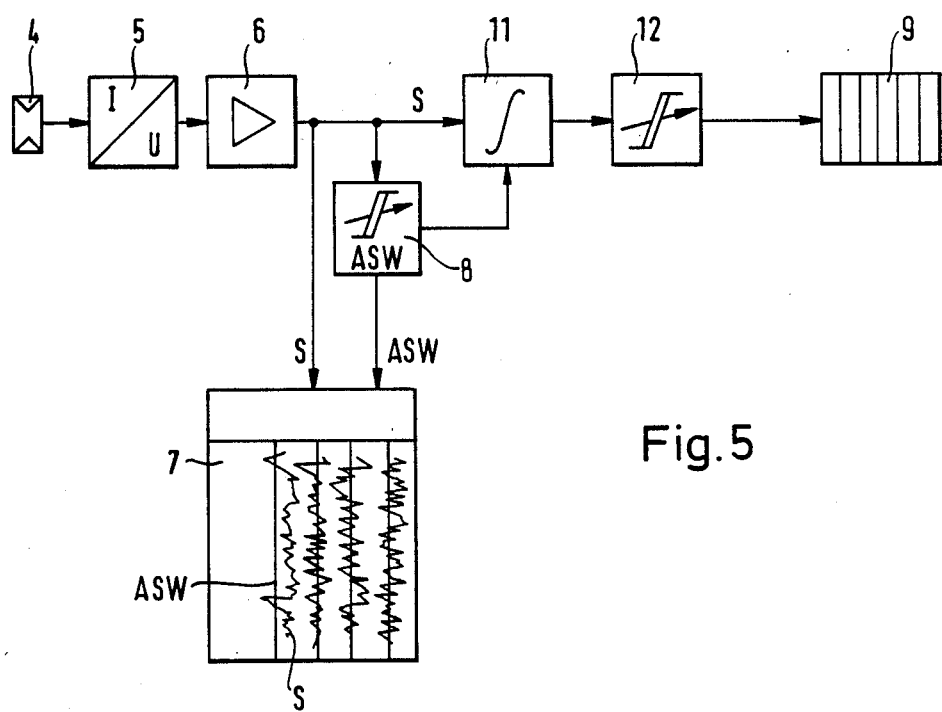
Figure 6:
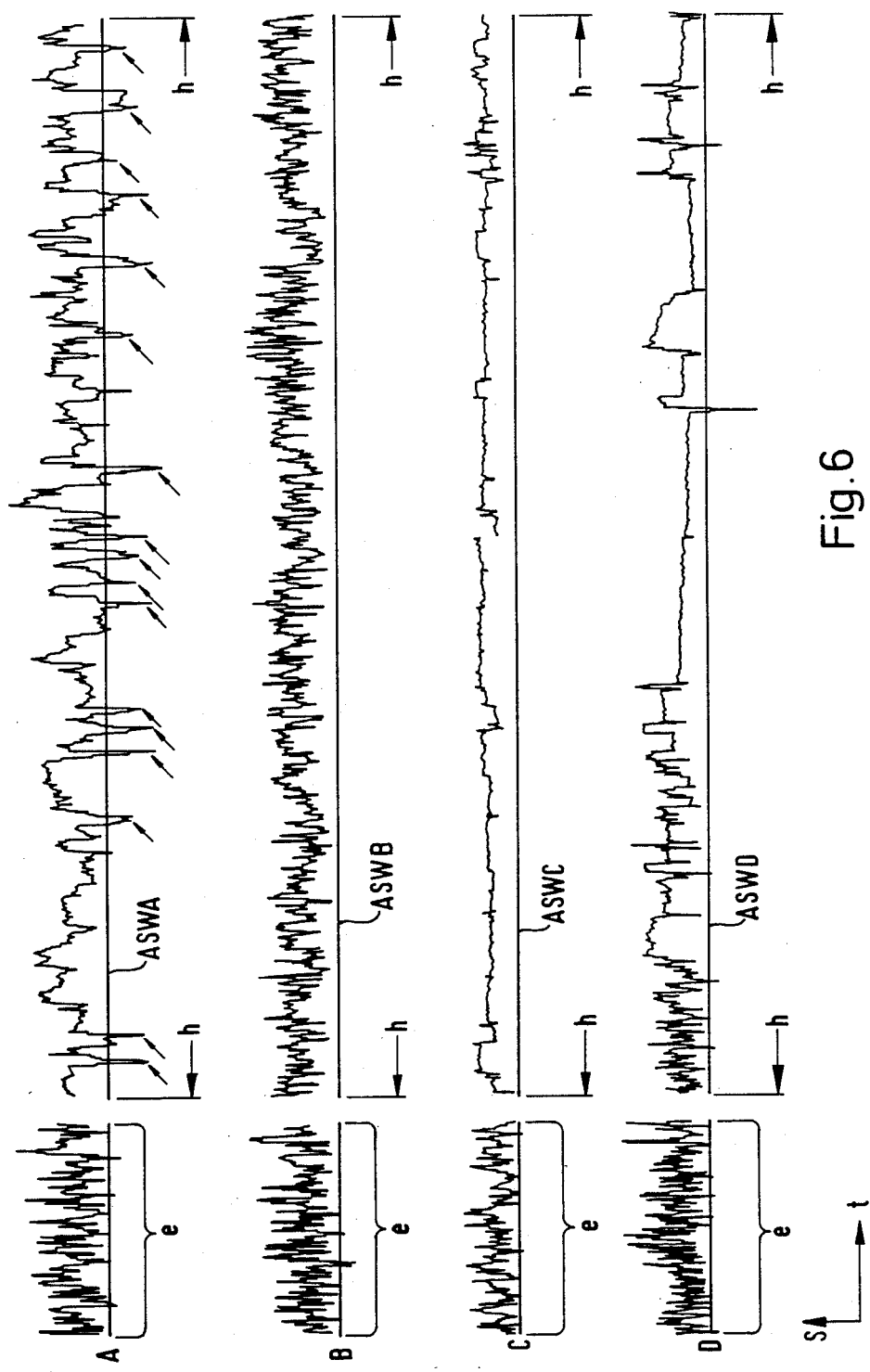
Figure 6A:
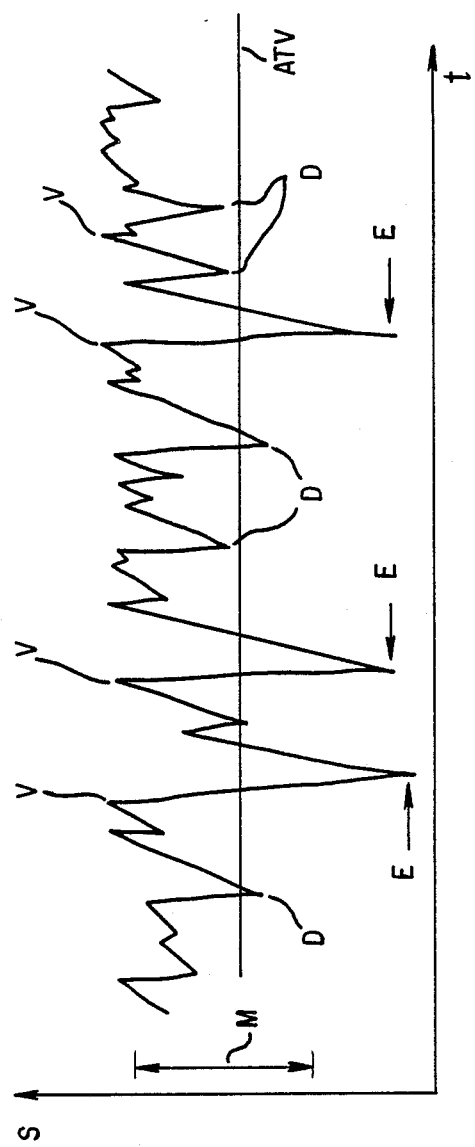

The invention will become more apparent from an example shown in the figures, wherein:

FIGS. 1a and 1b show schematic views of the principle according to the invention with two different positions of the experimental animal, FIG. 2 is a practical example of an operative embodiment of the principle displayed in FIGS. 1a, 1b, FIG. 3 is a section along the line III—III of FIG. 2, FIG. 4 is a circuit block diagram of a first example of and embodiment of the electronic evaluating circuit, FIG. 5 is a circuit block diagram of a second example of the embodiment of the electronic evaluating circuit, FIG. 6 depicts four test diagrams, FIG. 6a is an enlarged diagram of the curve segment e as shown in FIG. 6.

Figure 7:
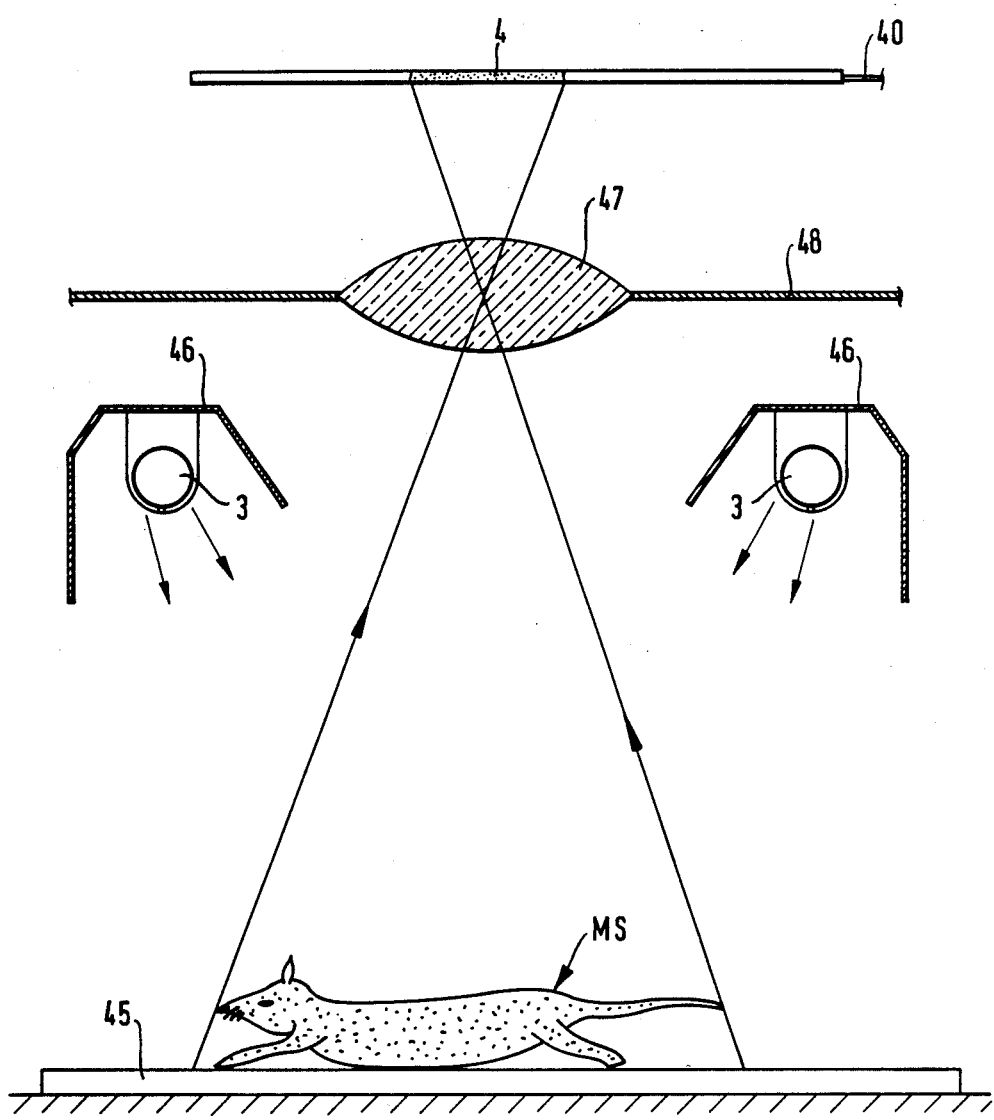
Figure 8:
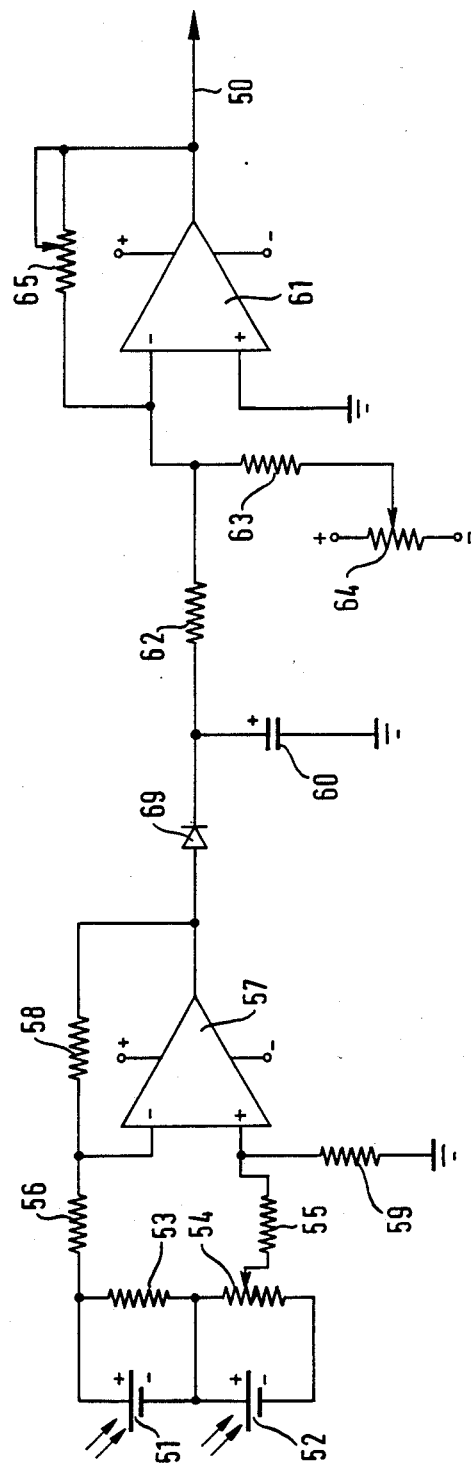

FIG. 7 is a schematic representation of the principle according to the invention, wherein in place of a shadow image, a projection image produced by optical means is detected, and FIG. 8 is an amplifier circuit for the coupling of the photoelements of the apparatus to a recorder, amplitude threshold detector or analog inlet of a computer used for recording and evaluation.

FIG. 1a and 1b show a mouse illuminated from above by a light source 3, in two different positions on a projection surface formed by a photoelement 4 and extending horizontally, i.e. at right angles to the direction of the force of gravity, wherein for the sake of simplicity a horizontally mounted transparent plate, to protect the photoelement 4 and support the mouse and which can be easily removed for cleaning, is not shown. FIG. 1a shows the mouse in its normal position MN and FIG. 1b in the stretching position MS. In the stretching position MS (FIG. 1b) the shadow outline of the mouse on the projection surface of the photoelement 4 is larger than in the MN position (FIG. 1a). The current emitted by the photoelement 4 through the cable 40 therefore declines whenever the mouse stretches (the decrease in the circumference of the body of the mouse is negligible). The evaluation of the signal emitted through the cable 40 is explained in detail later below. It is effected by the according of the movements in a memory device and/or by the counting of the relevant stretching movements by means of an evaluating circuit or a programmable computer.

In the practical apparative example of embodiment of FIGS. 2 and 3, in a housing 20 provided on top with air holes 22, four identical individual animal cages 1a, 1b, 1c and 1d are arranged. Each of these cages has a transparent bottom 25, under which the photoelement projection surface 4a, 4b, 4c and 4d are located. The cages 1a to 1d are covered on top with a glass plate 26 and are equipped laterally with air holes 27. The upper section of housing 20 also contains fluorescent tubes 30 with reflectors 31 positioned relative thereto. The housing 20 may be closed with a flap 21 on the operating side. Solar cells are preferably used as the photoelements 4a–d, wherein for example two solar cells may be connected to cover a bottom area larger than the area of a single solar cell.

The current supplied by the photoelements 4a to 4d flows through the wires 40a to 40d to the evaluating circuit according to FIG. 4 or 5, of which the first stage contains an amplifier circuit according to FIG. 8.

In FIGS. 4 and 5 the photoelement 4 is again shown in a symbolic manner. In both of the layouts the signal supplied by the photoelement 4 is conducted through a current/voltage converter 5 and an amplifier 6 on the one hand to a recorder 7 and on the other, to an amplitude threshold value detector 8, with a threshold value ATV that may be adjusted in keeping with the prevailing experimental conditions. The empirically or automatically determined and adjusted amplitude threshold value ATV is passed to the recorder 7 and recorded therein together with the signal S supplied by the amplifier 6.

According to the circuit layout of FIG. 4, the output of the amplitude threshold detector 8 is connected by means of a selectively adjustable time interval threshold value detector 10 with a counter 9 having a permanently set counting period. The counter counts within the predetermined time period of 10 min all of the states in which the signal S is lower for a certain minimum duration of for example 1.3 sec determined by the time interval threshold value detector 10 than a certain lower value set by the amplitude threshold value detector 8 (large shadow=small current=low voltage="small" signal S).

According to the circuit layout of FIG. 5, the output of the amplifier 6 is connected with resettable integrator 11, controlled by the amplitude threshold detector 8 in a manner such that the signal S supplied by the amplifier 6 is always integrated over the time intervals during which he signal S is lower than the amplitude threshold value ATV and the integrator 11 is reset immediately afterwards. The output of the integrator 11 is connected to counter 9 through an integral amplitude threshold value detector 12 also having an adjustable threshold value. The counter 9 thus counts within a certain period of time the states in which the integral values exceed the threshold value preset on the integral amplitude threshold value detector 12.

The evaluating circuits of FIG. 4 or 5 are multichannel in actual practice. For the cage layout of FIG. 2 and 3 four channels are required (with all of the cages occupied).

FIG. 6 shows printout of a four-channel recorder connected to the evaluating circuit according to FIG. 4 or 5 or respectively the stages shown in FIG. 8.

The amplified signals S produced by the movements of the four experimental animals A to D are recorded in the traces A to D.

Prior to the onset of the recording (of the signal S), the animals are given the different substances to be compared. Animal A (control animal) remains untreated; it receives the solvent only (water in most cases). In the present experiment Animals B to D are given the following substances:

B=antiphlogistic (Voltaren®)
C=analgetic (morphine)
D=stimulant (amphetamine).

The curve segments e show the so-called prerun (duration approximately 2 min), during which the effect on the behaviour of the animals of the test substance administered approximately 10 min earlier is recorded. The prerun is used to determine the amplitude threshold value, which subsequently (main run) represents the criterion for identifying stretch movements. As a rule, the amplitude threshold value ATV is determined as the mean value of, for example, the 3rd to 10th highest deflections (downward). This threshold value ATVA to ATVP (for each animal individually or identically for all animals) is then set manually on the threshold value detector 8 for each channel, or else, if a computer is used, determined by an evaluating program and used in the processing of the signal S in the computer.

A comparison of the curve segments e of the curves B, C and D with the segment e of the curve A shows the following: B Voltaren® has no effect on motility; C a slight sedating effect of morphine; D an increase in frequency, a central nervous side effect of amphetamine.

At the completion of the prerun e, all animals were injected with the irritant phenyl-p-benzoquinone in the peritonium (Hendershot and Forsaith, Journal Pharmacol. Exp. Therap. 125, 237, 1959). The effect on the individual animals is shown by the segments h (main test) of the curves A–D (duration approximately 10 min each).

The curve A (control animal without an inhibiting substance) is lower in the segment h than the threshold value ATVA altogether 24 times, while the curves for experimental animals B and C are not under the threshold value ATVB and ATVC in the segment h, and the curve for animal D is lower four times than the threshold value ATVD. However, only curve points exceeding the threshold value which are passed by the time interval value detector 10 to the counter 9 are viewed as significant. If this threshold value is set for example at approximately 0.5 sec. to 4 sec., and preferably 1.5 sec (empirically determined optimum value), then for the control animals A seventeen significant lower values or significant stretches are identified, none for the experimental animals B and C and two for the animal D. In FIG. 6 all significant lower values all indicated by arrows.

It may be "read" from the curves that the peripherally acting Voltare ® (animal/curve B) protects completely against pain (curve B: zero number of significant stretches in the curve segment h), without affecting motility (curve B: the segments e and h are nearly identical relative to amplitude and frequency). On the other hand, centrally acting substances affect the motility. Centrally acting analgesics have a slight sedating effect and reduce the motility (animal/curve C: morphine, amplitudes and frequencies lower). Stimulating substances cause central-nervous side effects with altered motilities (animal/curve D: amphetamine, higher frequencies in segment e).

In the example of embodiment shown in FIG. 7 of the invention, in a deviation from the layout of FIGS. 1a and 1b, the photoelement 4 which again may consist of one or several large area solar cells, is located above the mouse MS shown in the stretched position. In FIG. 7, two fluorescent lamps 3 serve to illuminate the mouse MS and a bottom plate 45 which is of a color as different from that of the mouse MS as possible in order to create a high contrast scene. Shields 46 around the fluorescent lamps 3 prevent the direct incidence of the light emanating from the fluorescent lamps 3 onto the photoelement 4. Optical means 47 allows for the production of a sharp image of mouse MS on photoelement 4. The optical means 47 are shown in FIG. 7 schematically together with a shield 48. Corresponding to the photoelement 4 in FIGS. 1a and 1b, the photoelement 4 in FIG. 7 is connected by a wire 40 to the evaluating circuit according to FIG. 4 and 5 and by means of an amplifier circuit according to FIG. 8, with a computer. The image of the mouse MS produced on the photoelement 4 corresponds to the shadow image that may be created with a layout according to FIG. 1a and 1b, but wherein to obtain a high signal/noise ratio a good color contrast between the mouse MS and the bottom plate 45 is required.

FIG. 8 shows an amplifier circuit corresponding to the current/voltage converter 5 and the amplifier 6 in FIG. 4 and 5. While in FIG. 4 and 5 the output 50 of the amplifier circuit feeds in addition to the recorder 7, a fixedly wired evaluating circuit with hard ware components, the amplifier circuit according to FIG. 8 is connected in keeping with a further example of embodiment of the invention directly with the inlet of an analog channel of a computer, said computer having other inlet channels to which appropriate amplifier circuits are connected.

The signal S standing at the outlet 50 is digitalized in the computer and evaluated under the control of the evaluating program in a manner corresponding to the functioning of the circuits according to FIG. 4 and 5.

The algorithm of the program to detect relevant stretchings provides that the shadow signal is taken up during 2 min in a prerun and then detected and evaluated for 10 min for the experimental run. The scanning of the signal is effected with ten values per second with a resolution of 12 bit. The measured values are stored during the measurements in the program and evaluated at the end of the experiment. The computer comprises a floppy disk station which makes it possible to selectively store on the disk either the results of the evaluation or additionally the measuring signal itself.

In FIG. 6a, the diagram of the test prerun, the curve segment e is shown on an enlarged scale. From the data of the prerun, by means of the computer program, a reference level corresponding to the threshold value of the amplitude threshold detector 8 is determined for the detection of stretches occurring during the experimental run following he prerun. For the purpose, the variation of the signal is examined during the prerun for maximum downward deflection D. If the difference of a maximum downward deflection D to the preceeding upward deflection V equals or exceeds a chosen value M, this maximum downward deflection is considered as an extreme value E and is excluded from further consideration. The amplitude threshold value ATV is then determined as the mean value of the 6th to 10th maximum downward deflections, with exclusion of the extreme values.

The algorithm for the detection and determination of the stretches provides that the signal at the outlet 50 is lower than the threshold value for a minimal period of time. The area included by the signal and the threshold value must be larger than the area of a rectangle of the same length and a predetermined minimal height.

As mentioned above, the first stages of the evaluating circuits according to the FIG. 4 and 5 correspond to the amplifier circuit according to FIG. 8. The amplifier circuit according to FIG. 8 is connected with two solar cells 51, 52 in series. The joining of the solar cells 51, 52 makes it possible to obtain a field of vision having an area larger than the area of a single solar cell 51 or 52. In order to equalize differences in sensitivity between the solar cells 51 and 52, the solar cell 51 is bridged with a buffer resistance of for example 10 Ohm and the solar cell 52 with a potentiometer 54 having a resistance of for example 500 Ohm. By shifting the take-off of the potentiometer 54, differences of the solar cells 51, 52 may be equalized.

The take-off of the potentiometer 54 and the end of the buffer resistance 53 facing away from the potentiometer 54 are connected by means of the respective 55 and 56 with the noninverting inlet and the inverting inlet of an operational amplifier 57. The resistivity values of the resistances 55 and 56 are equal. To adjust the amplification of the symmetrically operating amplifiers, identical coupling resistances 58 and 59 are provided, the resistivity values amounting to a multiple of the resistances 55 and 56.

As seen in FIG. 8, the outlet of the operational amplifier 57 is connected through a diode 69 with an electrolyte capacitor 60. The structural parts are dimensioned in a manner such that when the solar cells 51, 52 are exposed to light in the absence of a shadow produced by experimental animals, a voltage of 4.2 Volt appears at the electrolyte capacitor. The time constant determined by the electrolyte capacitor 60 is preferably less than one second, but large enough so that the intensity fluctuations of the fluorescent lamps 3 no longer interfere in the form of a superposed ac current signal. When the areas of the solar cells 51, 52 are shadowed more or less by an experimental animal, the voltage at the electrolyte capacitor 60 decreases, thereby smoothing the signal.

The voltage standing at the electrolyte capacitor 60 arrives through a coupling resistance 62 at an impedance converter containing the operational amplifier 61 corresponding to the operational amplifier 57. The inverting inlet of the operational amplifier 61 connected with the coupling resistance 62 is also connected by means of the resistance 63 with the take-off of a potentio-meter 64, from which a superposed voltage derived from the operating voltages may be taken off in order to effect a zero point setting. The inverting inlet of the operational amplifier 61 is further connected through a potentiometer 65 with the outlet of the operational amplifier 61. The potentiometer 65 serves to adjust the amplification. The noninverting inlet of the operational amplifier 61 is grounded as may be seen in FIG. 8.

The amplifier circuit shown in FIG. 8 thus forms together with a solar cell 51 or with two solar cells 51, 52 connected by means of a correcting circuit, an extremely simple circuit for the determination of the motility of an experimental animal, wherein it is possible to detect a plurality of shadow areas of different size, without the occurrence of signal jumps due to photodetectors associated with a plurality of discrete individual image points requiring extensive signal processing and reducing the resolution ability as the result of discretization into a plurality of image points.

We claim:

1. Apparatus for the recording and/or evaluation of the writhing behaviour of experimental animals, comprising an animal cage which is entered from above by the light of a light source, having a bottom (25) of the cage (1) which is light permeable and extends horizontally, electric detection means (4) positioned under the bottom (25) provided to form a projection surface or that the photoelectric detection means constitutes the bottom of the cage, the photoelectric detection means (4) comprising a single solar cell (51) covering approximately all of the area of the projection surface or of the bottom of the cage and being electrically connected via an amplifier (6) with a signal recording device (7) and/or an evaluating device (8, 9, 10, 11, 12).

2. Apparatus according to claim 1, wherein the photo electric detection means (4) is electrically connected via the amplifier (6) and an amplitude threshold value detector (8) having an adjustable threshold value (ATV), with a counter (9).

3. Apparatus according to claim 2, wherein the signal recording device is a signal recorder (7) electrically connected with the amplitude threshold value detector (8) in a manner such that it also records the set amplitude threshold value (ATV).

4. Apparatus according to claim 2, wherein the amplitude threshold value detector (8) is electrically connected via a time interval threshold value detector (10) with the counter (9).

5. Apparatus according to claim 2, wherein the amplitude threshold value detector (8) is connected by means of an integrator (11) and a subsequent integral threshold value detector (12) with the counter (9).

6. Apparatus according to claim 1, wherein several cages (1) together with their photo electric detection means (4) are located in a housing (20), in the upper part whereof a common light source is arranged for all of the cages (1).

7. Apparatus according to claim 6, wherein the signal recording device (7) is a multiple signal recorder having a plurality of inputs and each of the photo electric detection means (4) is electrically connected with one of said inputs.

8. Apparatus according to claim 1, wherein the multiple signal recording device and the evaluating device comprise a computer whereby the signals fed in by means of an amplifier circuit may be analyzed.

9. Apparatus for the recording and/or evaluation of the writhing behaviour of experimental animals with an internally illuminated animal cage, the bottom area whereof may be reproduced by means of an optical device on a photoelectric detection means located at a distance from the bottom of the cage which is electrically connected via an amplifier with a signal recording device and an evaluating device or one of the two alternatively, and whereby a signal may be produced as a function of the movements of an experimental animal kept in the cage, to record and evaluate the writhing behaviour of said animal, and wherein the photoelectric detection means (4,) comprises a single, large area solar cell (51) homogeneously covering the image areas of the optical device.

10. Apparatus according to claim 9, wherein the photo electric detection means (4) is electrically connected with a counter (9) via the amplifier (6) and an amplitude threshold value detector (8) having an adjustable threshold value (ATV).

11. Apparatus according to claim 10, wherein the signal recording device is a signal recorder (7) electrically connected with the amplitude threshold value detector (8) in a manner such that it simultaneously also writes the amplitude threshold value (ATV).

12. Apparatus according to claim 10, wherein the amplitude threshold value detector (8) is electrically connected via a time interval threshold detector (10) with the counter (9).

13. Apparatus according to claim 10, wherein the amplitude threshold value detector (8) is connected by means of an integrator (11) and a subsequent integral threshold value detector (12) with the counter (9).

14. Apparatus according to claim 9, wherein several cages (1) together with their respective photo electric detection means (4) are located in a housing (20), in the upper part whereof a common light source is arranged for all of the cages (1).

15. Apparatus according to claim 14, wherein the recorder (7) is a multiple signal recorder having a plurality of inputs and each photo electric detection means (4) is electrically connected with one of said inputs.

16. Apparatus according to claim 9, wherein the multiple signal recorder and the evaluating device comprise a computer, whereby the signals fed in through an amplifier circuit may be analyzed.

17. Process for the recording and/or evaluation of the writhing behavior of experimental animals, wherein radiation is directed at the animal which is absorbed and/or reflected at least in part by the body of the animal, an image of the animal body is produced on a projection surface and, by a single areal photoelectric detection means of constant sensitivity across its area homogeneously extending across the projection surface, a signal is generated photoelectrically and recorded, which is a continuous function of the size of the image.

18. Process according to claim 17, wherein the radiation is applied from above and the projection surface is located under the animal supported on a horizontal plane, so that a shadow image of the animal essentially reproducing the body of the animal on said projection surface is produced.

19. Process according to claim 17, wherein a threshold value of the amplitude is determined for the signal and, within a predetermined counting period, the number of instances when said signal drops below said amplitude threshold value is counted.

20. Process according to claim 17, wherein a threshold value of the amplitude is determined for the signal and a time interval threshold value is determined for the time intervals wherein the signal is below said amplitude threshold and within a predetermined counting period the number of instances in which the signal drops below the amplitude threshold value and simultaneously exceeds the time interval threshold value is counted.

21. Process according to claim 17, wherein the signal is integrated always over the time intervals during which it is below a certain amplitude threshold value; that for these integrals an integral threshold value is determined, and that within a certain period of time the number of instances wherein the integrals exceed the integral threshold value is counted.

22. Process according to claim 20, wherein the amplitude threshold value is set and determined in keeping with the prevailing experimental conditions, by that during a prerun the mean value of a certain number of the largest signal downward deflections is determined with the exclusion of a smaller number of said largest signal downward deflections.

23. Process according to claim 21, wherein the integral threshold value is set and determined in keeping with the prevailing experimental conditions, by forming the mean value in the course of a prerun of a certain number of the largest signal downward deflections, with the exclusion of a certain smaller number of the largest of said signal downward deflections.

24. Process according to claim 20, wherein the time interval threshold value is set for approximately 0.5 sec to 4 sec.

* * * * *